(12) United States Patent
Schlereth et al.

(10) Patent No.: US 9,194,685 B2
(45) Date of Patent: Nov. 24, 2015

(54) RETRACTABLE ASSEMBLY

(71) Applicant: Endress + Hauser Conducta Gesellschaft für Mess-und Regeltechnik mbH + Co. KG, Gerlingen (DE)

(72) Inventors: Rainer Schlereth, Neuss (DE); Stefan Robl, Hunxe (DE); Alejandro Vaca Torres, Steinheim (DE); Martin Lohmann, Gerlingen (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 187 days.

(21) Appl. No.: 13/898,969

(22) Filed: May 21, 2013

(65) Prior Publication Data

US 2013/0314076 A1  Nov. 28, 2013

(30) Foreign Application Priority Data

May 22, 2012  (DE) .......................... 10 2012 104 412

(51) Int. Cl.
    *G01B 7/00* (2006.01)
    *G01N 27/28* (2006.01)
    (Continued)

(52) U.S. Cl.
    CPC .............. *G01B 7/003* (2013.01); *G01D 11/245* (2013.01); *G01N 27/283* (2013.01)

(58) Field of Classification Search
    CPC ..... G01B 7/003; G01D 11/245; G01N 27/283
    USPC ............... 324/207.13, 207.2, 207.21, 207.22, 324/207.23, 207.26
    See application file for complete search history.

(56) References Cited

U.S. PATENT DOCUMENTS 4,837,539 A * 6/1989 Baker ........................... 335/207
5,019,782 A * 5/1991 Schatter ........................ 324/655
(Continued)

FOREIGN PATENT DOCUMENTS

DE    1964139      2/1971
DE    9406884.4    9/1994
(Continued)

OTHER PUBLICATIONS

Porat FR 2027132 (A1) (English Machine Translation); "Electric unit for liquid level indication"; Published Sep. 25, 1970.*
(Continued)

*Primary Examiner* — Melissa Koval
*Assistant Examiner* — Felicia Farrow
(74) *Attorney, Agent, or Firm* — Bacon & Thomas, PLLC

(57) ABSTRACT

A retractable assembly for immersion-, flow- and annex-measuring systems in analytical process technology for measuring at least one measured variable of a medium in a process containment, comprising an essentially cylindrical housing having a housing interior; an immersion tube, which is axially movable between a retracted service position in the housing and a process position extended from the housing. In the service position, the immersion tube is positioned in the housing interior; a closure element on an end region of the immersion tube facing the medium for sealing off the housing interior from the process containment when the immersion tube is located in the service position, and a proximity detector in or on the end region of the housing facing the medium for detecting the closure element in the service position.

13 Claims, 2 Drawing Sheets

(51) Int. Cl.
*G01D 11/24* (2006.01)
*G01B 7/14* (2006.01)
*G01R 33/06* (2006.01)
*H01L 43/06* (2006.01)
*G01B 7/30* (2006.01)

(56) References Cited

U.S. PATENT DOCUMENTS

| | | | |
|---|---|---|---|
| 6,926,814 | B2 | 8/2005 | Koenemann |
| 2005/0264302 | A1* | 12/2005 | Mohajer et al. ............... 324/639 |
| 2009/0214387 | A1* | 8/2009 | Straub et al. ............... 422/82.01 |
| 2010/0109882 | A1* | 5/2010 | Lohmann et al. ............. 340/584 |
| 2011/0189050 | A1* | 8/2011 | Schlereth et al. ............... 422/28 |
| 2012/0055320 | A1* | 3/2012 | Morong .......................... 84/746 |
| 2013/0036843 | A1* | 2/2013 | Pfauch et al. ................ 73/866.5 |

FOREIGN PATENT DOCUMENTS

| | | |
|---|---|---|
| DE | 102010001391 A1 * | 8/2011 |
| EP | 1248102 A1 | 10/2002 |
| WO | 2004023127 A1 | 3/2004 |
| WO | 2008077714 A1 | 7/2008 |

OTHER PUBLICATIONS

German Search Report, Munich, Apr. 19, 2013.

* cited by examiner

RETRACTABLE ASSEMBLY

TECHNICAL FIELD

The invention relates to a retractable assembly for immersion-, flow- and annex-measuring systems especially in analytical process technology for measuring at least one measured variable of a medium in a process containment.

BACKGROUND DISCUSSION

Retractable assemblies are available from the group of firms, Endress+Hauser, in a large number of variants, for example, that bearing the designation "Cleanfit H CPA475".

Retractable assemblies are widely used in analytical measurements technology. They serve for introducing and removing probes to and from a process and its media without process interruption. The probes are secured to an immersion tube and, by means of a drive, moved manually or automatically, for example, pneumatically, axially between a process position and a service position. These events happen within a certain timing cycle or as a function of other determinable or measured parameters.

Probes in the sense of this invention comprise probes with at least one accommodation for at least one sensor for measuring one or more physical or chemical, process variables.

The fields of use of retractable assemblies for measuring physical or chemical, process variables of a medium, e.g. a fluid, especially a liquid, in process technology are many. Sensors are used for determining the process variables, wherein the sensors can be, for example, pH-sensors, conductivity sensors, optical or electrochemical sensors for determining a concentration of a substance contained in the medium to be monitored, e.g. $O_2$, $CO_2$, certain types of ions, organic compounds, etc.

The assembly, e.g. retractable assembly, represents an important part of the investment- and operating costs of a measuring point. The assembly accommodating the sensor is always contacting the medium and, thus, highly safety relevant. The assembly is the connection to the process. A lack of sealing and the then necessary repair of the assembly lead to process interruption. Dependent on the process medium, a defective assembly can endanger humans and the environment.

If retractable assemblies are used for accommodating the sensor for determining at least one process variable, the sensor can be checked, calibrated, cleaned and/or replaced in the service position, wherein the sensor is, in such case, located in a treatment chamber arranged in the housing of the retractable assembly.

"Above" and related terms mean, in the sense of this invention, remote from the medium. "Below" and related terms mean, in the sense this invention, toward the medium.

The reaching of the service position is recognized by the striking of the immersion tube on an upper stop on the housing remote from the medium. In the case of automatic retractable assemblies, there are variants, in the case of which the achieved position of the immersion tube in the service position is reported to a control unit by a reporter using an end position switch; see, in this connection, the already mentioned CPA475.

In the service position, the solid lower end of the immersion tube seals off from the process (the medium). Thus, there is a seal between the process containment and the housing interior and therewith the sensor space. Only in this position, is it permitted that the assembly be opened, so that the sensor can be taken out, without, in such case, suffering the escape of process medium.

A secure sealing off of the process, thus the closing the process opening, is very important, since otherwise, in the case of opening the assembly, or the screwing out of the sensor for service purposes, process medium can escape through the immersion tube. In many cases, the process medium is under pressure. It can be hot, poisonous or corrosive. An unintended opening is highly endangering for humans and environment. For repair, the process must be stopped and the area, in given cases, cleaned and even decontaminated.

In the case of previously known retractable assemblies, the partitioning off of the process is only assumed from the fact that the immersion tube has retracted completely into the assembly, thus the upper edge of the immersion tube has reached the upper limit or the piston of the pneumatic drive has reached the end position, and, thus, the lower end of the immersion tube has as closure element sealed off the process. The upper position reporter detects only the raised position of the immersion tube.

In the case, in which the immersion tube or the thereon located closure element has broken off, indeed, an "immersion tube in service position" is detected, while, nevertheless, the lower region of the immersion tube is missing and the opening to the process is still open. If, in this case, the assembly is opened for sensor service, process medium rises through the immersion tube into the environment. This represents a great danger that damage will occur.

SUMMARY OF THE INVENTION

An object of the invention is, therefore, to provide a safe and correct detection of the sealing off of the process.

The object is achieved by a retractable assembly for measuring at least one measured variable of a medium in a process containment, comprising: an essentially cylindrical housing having a housing interior; an immersion tube, which is axially movable between a retracted service position in the housing and a process position extended from the housing, wherein, in the service position, the immersion tube is positioned in the housing interior; a closure element on an end region of the immersion tube facing the medium for sealing off the housing interior from the process containment when the immersion tube is located in the service position; and a proximity detector in or on the end region of the housing facing the medium for detecting the closure element in the service position.

In an embodiment, the proximity detector is a magnetic proximity switch, and the closure element has a permanent magnet. Especially, the magnetic proximity switch is a reed contact or a Hall-sensor.

In a variant, the proximity detector is an inductive proximity switch, and the closure element has a ferro- or ferrimagnetic element.

Especially, the inductive proximity switch is a coil, and the detecting of the closure element occurs via electromagnetic induction.

In a variant, the inductive proximity switch is an oscillator, especially an LC oscillator, having at least one resonant frequency, wherein its inductance determining the resonance frequency changes in the case of proximity of the closure element.

Alternatively, the proximity detector is a first oscillator, especially an LC oscillator, wherein there is provided in the closure element a second oscillator, which is so embodied that its resonant frequency essentially corresponds to the resonant frequency of the first oscillator, and an inductive power removal in the first oscillator detects proximity of the closure element.

In an additional variant, the proximity detector is a capacitive proximity switch, wherein an oscillator, especially an LC oscillator, is provided, whose frequency determining capacitance depends on the proximity of the closure element.

In an additional variant, the proximity detector is an electrical circuit, wherein the immersion tube carries an electrical circuit, which is interrupted in the case of damage to the immersion tube.

Alternatively, the proximity detector is a mechanical switch, wherein the closure element in the case of proximity activates the mechanical switch.

In an additional alternative, the proximity detector is a particle and/or radiation detector and the closure element has a radioactive element.

Furthermore, it is provided that the proximity detector is an RFID chip seated in the closure element and the proximity detector is embodied as a receiving coil, wherein the RFID chip and the receiving coil are so embodied that communication between the two is only possible when the immersion tube is located in the service position.

BRIEF DESCRIPTION OF THE DRAWINGS

The invention will now be explained in greater detail based on the appended drawing, the figures of which show as follows:

FIG. 2 is a cross section through the lower part of the retractable assembly as shown in FIG. 1a.

DETAILED DISCUSSION IN CONJUNCTION WITH THE DRAWINGS

Figure 1A:
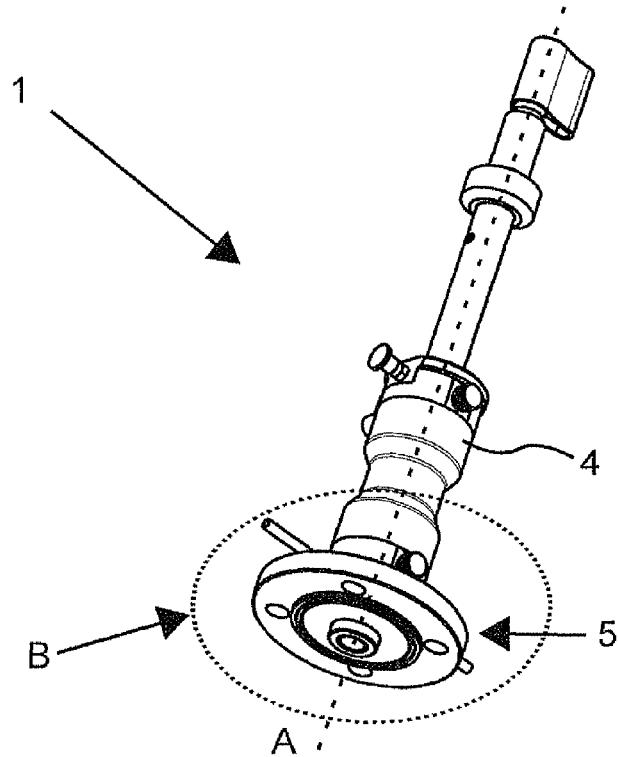
FIG. 1a is a retractable assembly in side view with the immersion tube in service position.

In the figures, equal features are provided with equal reference characters.

The retractable assembly of the invention in its totality is given the reference character 1. The retractable assembly 1 is composed of an essentially cylindrical housing 4, which can be connected by means of a connector 5 to a containment (not shown). In the example, the connector is a flange connector, e.g. one of stainless steel. Other embodiments are, however, possible. Located in the containment is the medium to be measured.

Figure 1B:
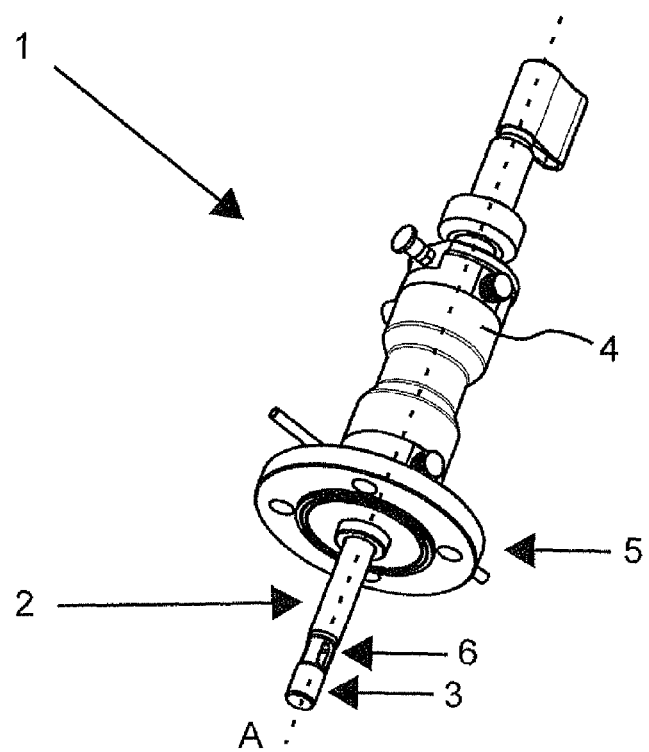
FIG. 1b is a retractable assembly in side view with the immersion tube in process position.

FIG. 1a shows the retractable assembly 1 in service position. FIG. 1b shows the retractable assembly 1 in process position. This is explained in the following in greater detail.

Guided within the housing 4 is an immersion tube 2. A probe (not described in greater detail) is connected with the immersion tube 2 by a holder (likewise not described in greater detail), for example, a holder with a threaded connector. The probe serves for determining one or more physical and/or chemical, process variables. Process variables, which can be registered with the probe, include, for example, pH-value, also via ISFET, redox potential, absorption of electromagnetic waves in the medium, for example, with wavelengths in the UV-, IR-, and/or visible region, oxygen, conductivity, turbidity, concentration of metal and/or nonmetallic materials and temperature. Via an opening 6 in the immersion tube 2, the probe, respectively the sensor, has access to the medium to be measured.

The immersion tube 2 is accommodated axially displaceably along the central axis A in the direction toward the containment, respectively in the direction away from the containment. Immersion tube 2 is, in such case, movable between the retracted service position in the housing 4 (FIG. 1a) and the process position extended from the housing 4 (FIG. 1b). In the process position, the measuring takes place, while, in the service position, the most varied of service tasks, such as cleaning and calibration, are performed. The shifting of the immersion tube 2 is effected by a manual or automatic, for example, pneumatic, hydraulic or electrical, drive. This is known from the state of the art and does not need to be further explained.

If the immersion tube 2 is located in service position, the immersion tube 2 is positioned in the housing interior 4.1. Located on the lower end of the immersion tube 2 is the closure element 3 for sealing off the process. The closure element 3 seals the housing interior 4.1 from the process, and therewith from the medium. The medium can be hot, poisonous, corrosive or in other manner harmful for humans and environment. It is, consequently, to be heeded that the closure element 3 seals safely and durably. For such purpose, different sealing systems are placed on the closure element 3; especially, sealing rings are used.

A safe maintenance of the sensor is, thus, only possible when is assured that the closure element 3 sits correctly against the lower end of the housing interior 4.1.

The immersion tube 2 can be produced from different materials. The state of the art includes immersion tubes 2 of steel, e.g. stainless steel. There are, however, applications, especially in the chemical industry, in the case of which very resistant materials are applied. The immersion tube 2 can, thus, also be produced of a synthetic material, such as Polyetheretherketone (PEEK) or some other synthetic material. According to definition, these materials are mechanically less stable and there is the danger of breakage, especially when the closure element 3 or the sealing rings on the closure element 3 swell in the process medium and, in traveling into the service position, tear off. It must be assured that such breakage can be detected, respectively it must be assured that the assembly is not opened when the immersion tube 2 with the closure element 3 is damaged.

Figure 2:
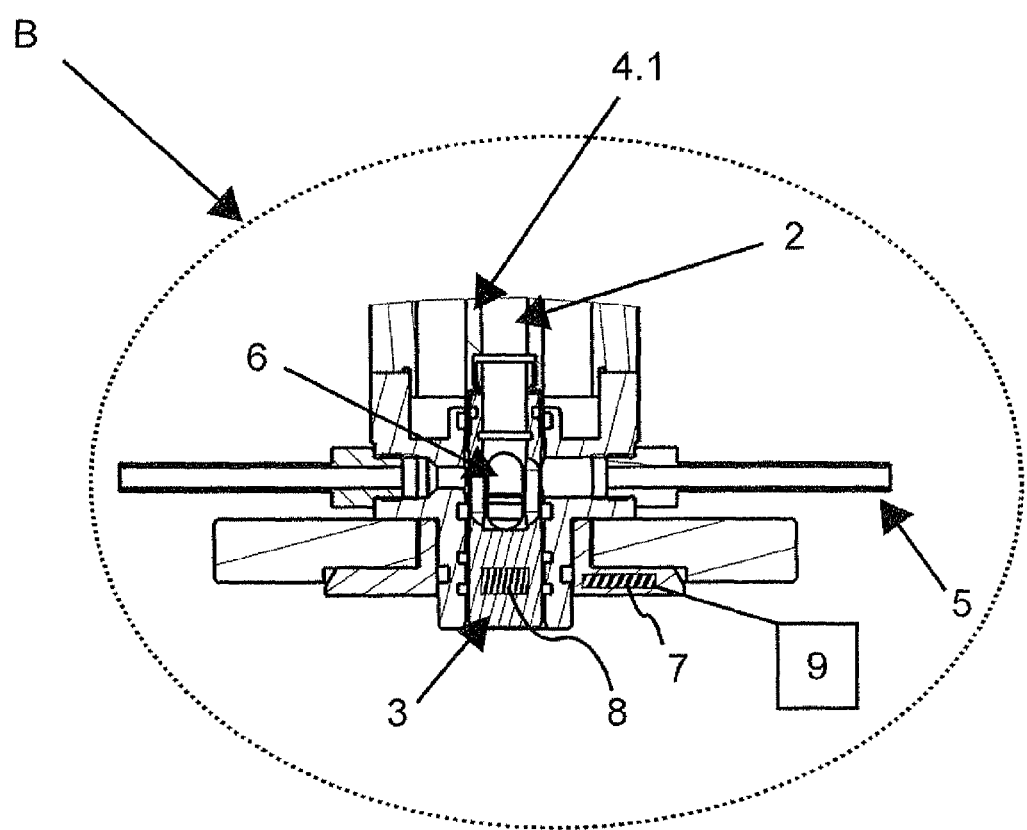

FIG. 2 shows the section B of FIG. 1a enlarged. Illustrated is the lower part of the retractable assembly 1 in cross section. Included is a proximity detector 7, which is provided in the lower end region of the housing 4. A counterpart suitable for the proximity detector 7, an initiator 8, is located in the closure element 3. Only when the proximity detector 7 detects the initiator 8 is it possible to open the assembly safely and without fear of damage and to service such. Not further detailed but absolutely necessary is an electrical connection of at least proximity detector 7 to an evaluation unit 9. This can be, for example, a measurement transmitter, which also evaluates the measurement data, but it can also be some other intelligent unit. Evaluation unit 9 detects the signals of the proximity detector 7 and decides whether the closure element 3, respectively the immersion tube 3, is already positioned in the housing interior 4.1, and therefore a servicing of the sensor is possible without danger.

Proximity detector 7 can be placed in a bore in the connector 5. The proximity detector 7 can also be adhered, cast, welded, etc. in place.

As already mentioned, the immersion tube 2 of a typical instance of application is composed of a resistant synthetic material. Initiator 8 can then be cast in the closure element 3.

Different combinations of proximity detector 7 and initiator 8 are possible, as is explained in greater detail in the following.

The proximity detector 7 can be a magnetic proximity switch, and the initiator can be embodied in the form of a permanent magnet. Detection happens then via a reed contact or a Hall sensor.

Also, the movement of the immersion tube 2 can be detected via magnetic induction when the initiator 8 is embodied in the form of a ferro- or ferrimagnetic element. In this case, the proximity detector 7 is embodied in the form of an electrical coil. If the proximity detector 7 is constructed in the form of an oscillator, especially in the form of an LC oscillator, then the inductance determining the resonance frequency can change in the case of proximity of the initiator 8 to the proximity detector 7 and, thus, the closure element 3 detected.

If not only the proximity detector 7 but also the initiator 8 are both formed as oscillators, especially as LC oscillators, and the resonance frequencies of the two are essentially equal, then the closure element 3 can be detected when the immersion tube 2 is located in service position, through inductive power removal in the oscillator.

In a variant, an option is that, through the movement, the capacitance of the oscillator changes and, thus, the resonant frequency shifts, which, in turn, can be measured.

In the simplest case, the proximity detector 7 is an electrical circuit. If for some reason, e.g. immersion tube fracture, the electrical circuit is interrupted, a report is output and corresponding measures can be introduced.

Furthermore, the closure element 3 can, upon movement in the housing interior 4.1, activate a mechanical switch. Only when this switch is moved from one position to the other does the intelligent unit permit opening of the retractable assembly.

In a variant, initiator 8 includes a weakly radioactive element, which is detected by a corresponding measuring apparatus, for example, a particle and/or radiation detector.

Furthermore, it is provided that the initiator 8 is in the form of an RFID chip and the proximity detector 7 is a receiving coil and they can only communicate with one another when the closure element 3 seals the process off.

The invention claimed is:

1. A retractable assembly for immersion-, flow- and annex-measuring systems in analytical process technology for measuring at least one measured variable of a medium in a process containment, comprising:
    an essentially cylindrical housing having a housing interior;
    an immersion tube, which is axially movable between a retracted service position in said housing and a process position extended from said housing, in the service position, said immersion tube is positioned in said housing interior;
    a closure element on an end region of said immersion tube facing the medium for sealing off said housing interior from the process containment when said immersion tube is located in the service position; and
    a proximity detector in the end region of said housing facing the medium for detecting said closure element in the service position.

2. The retractable assembly as claimed in claim 1, wherein:
    said proximity detector is a magnetic proximity switch, and said closure element has a permanent magnet.
3. The retractable assembly as claimed in claim 2, wherein:
    said magnetic proximity switch is a reed contact.
4. The retractable assembly as claimed in claim 2, wherein:
    said magnetic proximity switch is a Hall-sensor.
5. The retractable assembly as claimed in claim 1, wherein:
    said proximity detector is an inductive proximity switch, and said closure element has a ferro- or ferrimagnetic element.
6. The retractable assembly as claimed in claim 5, wherein:
    said inductive proximity switch is a coil, and the detecting of said closure element occurs via electromagnetic induction.
7. The retractable assembly as claimed in claim 5, wherein:
    said inductive proximity switch is an oscillator, especially an LC oscillator, having at least one resonant frequency, wherein its inductance determining the resonance frequency changes in the case of proximity of said closure element.
8. The retractable assembly as claimed in claim 1, wherein:
    said proximity detector is a first oscillator, especially an LC oscillator;
    a second oscillator in said closure element, whose resonant frequency essentially corresponds to the resonant frequency of the first oscillator; and
    an inductive power removal in the first oscillator detects proximity of said closure element.
9. The retractable assembly as claimed in claim 1, wherein:
    said proximity detector is a capacitive proximity switch;
    an oscillator, especially an LC oscillator, is provided, whose frequency determining capacitance depends on the proximity of said closure element.
10. The retractable assembly as claimed in claim 1, wherein:
    said proximity detector is an electrical circuit; and
    said immersion tube carries an electrical circuit, which is interrupted in the case of damage to said immersion tube.
11. The retractable assembly as claimed in claim 1, wherein:
    said proximity detector is a mechanical switch; and
    said closure element in the case of proximity activates said mechanical switch.
12. The retractable assembly as claimed in claim 1, wherein:
    said proximity detector is a particle and/or radiation detector; and
    said closure element has a radioactive element.
13. The retractable assembly as claimed in claim 1, wherein:
    said proximity detector is an RFID chip seated in said closure element; and
    said proximity detector is embodied as a receiving coil, wherein the RFID chip and the receiving coil are so embodied that communication between the two is only possible when said immersion tube is located in the service position.

* * * * *